United States Patent [19]

Pope

[11] 4,303,794
[45] Dec. 1, 1981

[54] SEPARATION AND RECOVERY OF 4,4'-METHYLENE DIMETHYL DIPHENYLDICARBAMATE

[75] Inventor: Brian G. Pope, Baton Rouge, La.

[73] Assignee: The Dow Chemical Company, Midland, Mich.

[21] Appl. No.: 219,146

[22] Filed: Dec. 22, 1980

[51] Int. Cl.$^3$ .......................................... C07C 125/073
[52] U.S. Cl. ...................................................... 560/25
[58] Field of Search ......................................... 560/25

[56] References Cited

U.S. PATENT DOCUMENTS

| | | | |
|---|---|---|---|
| T994,004 | 5/1980 | Shawl | 560/25 |
| 2,517,965 | 8/1950 | Bohl . | |
| 2,527,240 | 10/1954 | Baird | 260/404.5 |
| 2,946,768 | 7/1960 | Klauke et al. | 560/25 |
| 4,162,362 | 7/1979 | Shawl | 560/25 |
| 4,163,019 | 7/1979 | Mango | 260/453 AM |
| 4,172,948 | 10/1979 | Shawl | 560/25 |
| 4,243,815 | 1/1981 | Werger | 560/25 |

*Primary Examiner*—G. T. Breitenstein

[57] ABSTRACT

A method of separating 4,4'-methylene dimethyl diphenyldicarbamate from its 2,4' and 2,2'-isomers, from methyl phenylcarbamate, from higher phenylcarbamate derivatives, and from related compounds. The mixture is washed with methanol, thereby forming a liquid phase comprising a methanol solution of predominantly 2,4'-isomer, 2,2'-isomer, diphenyldicarbamate, methyl phenylcarbamate, and higher phenylcarbamate derivatives; and a solid phase of substantially 4,4'-methylene dimethyl diphenyldicarbamate. The 2,4'-isomer and 2,2'-isomer may also be separated by using a methanol-water solution wash.

17 Claims, No Drawings

4,303,794

SEPARATION AND RECOVERY OF 4,4'-METHYLENE DIMETHYL DIPHENYLDICARBAMATE

BACKGROUND OF THE INVENTION

This invention relates to a method for separating and recovering 4,4'-methylene dimethyl diphenyldicarbamate. More particularly, this invention relates to a method for separating and recovering substantially pure 4,4'-methylene dimethyl diphenyldicrbamate from a mixture of compounds including other methylene dialkyl diphenyldicarbamates, alkyl phenylcarbamates, higher phenylcarbamate derivatives, and related compounds.

The compound 4,4'-methylene dimethyl diphenyldicarbamate, hereinafter referred to as 4,4'-MDDC, which is an intermediate in the production of 4,4'-methylene diphenyldiisocyanate, hereinafter referred to as 4,4'-MDI, can be made by the condensation reaction of formaldehyde and methyl phenylcarbamate, hereinafter referred to as MPC. The 4,4'-MDDC can then be thermally decomposed to produce 4,4'-MDI, which is a particularly useful intermediate in the production of polyurethanes. It is accordingly important to provide a method of separating relatively pure 4,4'-MDDC from byproducts and intermediates of the condensation reaction and from unreacted MPC. The present invention provides such a method.

SUMMARY

In general, this invention provides a method for the separation of a reaction product, 4,4'-methylene dimethyl diphenyldicarbamate; a reactant, methyl phenylcarbamate; byproduct compounds, or reaction intermediates in the condensation reaction of methyl phenylcarbamate and formaldehyde; other methylene dialkyl diphenyldicarbamates, and other phenylcarbamates. This method comprises the steps of (a) washing a mixture, including the methyl phenylcarbamate reactant, byproduct compounds, reaction intermediates, other methylene dialkyl diphenyldicarbamates, or other alkyl phenylcarbamates, and the 4,4'-methylene dimethyl diphenyldicarbamate product, with an alcohol having less than four carbon atoms per molecule, thereby forming a liquid phase which includes the alcohol and the compounds in the mixture which are soluble in the alcohol, and a solid phase which is substantially 4,4'-methylene dimethyl diphenyldicarbamate product; and (b) separating the solid and liquid phases.

The present invention is based on differences in solubility in the lower aliphatic alcohols. Since 4,4'-methylene dimethyl diphenyldicarbamate is virtually insoluble in the lower alcohols, it may be separated from compounds which are soluble therein by washing a mixture of 4,4'-methylene dimethyl diphenyldicarbamate and alcohol-soluble compounds with one or more of these alcohols. Compounds soluble in the lower alcohols include 2,4'-methylene dimethyl diphenyldicarbamate (2,4'-MDDC), 2,2'-methylene dimethyl diphenyldicarbamate (2,2'-MDDC), alkyl phenylcarbamates, other methylene dialkyl diphenyldicarbamates, higher phenylcarbamate derivatives, and other byproducts and intermediates in the reaction of alkyl phenylcarbamates with formaldehyde.

When the alcohol is methanol, a mixture of methanol and water may be used in the wash step because of the high solubility of methanol. Furthermore, it is possible to first wash a mixture of reactants, intermediates, byproducts, reaction products and other alkyldicarbamates with a methanol/water mixture, containing a high percentage of water, to separate out a solid phase including the 2,4'-isomer and 2,2'-isomer, as well as the 4,4'-isomer. This mixed solid phase can then be further washed with increasingly pure alcohol to separate each of the isomers.

It is an object of this invenion to provide a method for the separation of 4,4'-methylene dimethyl diphenyldicarbamate from its isomers, from other methylene dialkyl diphenyldicarbamates, from alkyl phenylcarbamates, from higher phenylcarbamate derivatives, and from other related compounds. It is another object of this invention to provide a method for the separation of 4,4'-methylene dimethyl diphenyldicarbamate, from 2,4'-methylene dimethyl diphenyldicarbamate, from 2,2'-methylene dimethyl diphenylcarbamate, and from other methylene dialkyl diphenyldicarbamates, alkyl phenylcarbamates, higher phenylcarbamate derivatives, and other related compounds. It is still another object of this invention to provide methods therefor which are easy, convenient, rapid, efficient, and economical. It is a further object of this invention to provide methods therefor which do not require chemically changing any of the components of the mixture being resolved. It is a still further object of this invention to provide methods therefor which permit the facile recovery of all components of the mixture and of the alcohol used to resolve the mixture. These and other objects of the invention will be apparent to those skilled in the art from the more detailed description which follows.

DESCRIPTION OF THE PREFERRED EMBODIMENTS

The following description illustrates the manner in which the principles of the present invention are applied, but is not to be construed as in any sense limiting the scope of the invention.

More specifically, the method of this invention uses an alcohol with less than four carbon atoms per molecule to separate 4,4'-MDDC from a reaction mixture obtained from the condensation reaction between formaldehyde and MPC. The preferred alcohol is methanol. A typical reaction-product mixture comprises 4,4'-MDDC, 2,4'-MDDC, 2,2'-MDDC, unreacted MPC, higher phenylcarbamate derivatives, and other by-products and reaction intermediates.

The reaction mixture is washed with the alcohol, and the solid and liquid phases are separated by using any of the methods which are well known and commonly employed for making such separations. Examples of such separation techniques are sedimentation, decantation, filtration, and centrifugation. If methanol is used, the result is a solid phase of substantially pure 4,4'-MDDC, and a liquid phase comprising predominantly an alcohol solution of the other components of the original mixture. The temperature of the alcohol may be between about $-90°$ C. and about 60° C. Preferably, the temperature of the alcohol is between about 0° C. and about 25° C., and more preferably between about 10° C. and about 20° C. Preferably, the reaction mixture is predominantly 4,4'-MDDC and the weight of alcohol used is between about five and about ten times the weight of total solids in the mixture.

The separation can be made selective by choosing an alcohol other than methanol; or by the judicious use of water to dilute the methanol, thereby reducing its solvating power with respect to the alcohol-soluble compounds. To effect a multistage fractional separation, one begins with about a sixty percent methanol - forty percent water solution by volume for the initial wash step, increases the methanol concentration for each subsequent wash step, and makes the final wash with undiluted methanol. When using this embodiment of the invention, the alcohol is diluted with water to provide solutions which preferably comprise between about sixty percent and about ninety percent alcohol and between about ten percent and about forty percent water by volume. Alternatively, one may use undiluted n-propyl or isopropyl alcohol for the initial wash step, undiluted ethanol for the intermediate wash step, and undiluted methanol for the final wash step. The mode comprising the use of methanol-water solutions is preferred, because the separation of several alcohols is thereby avoided.

The temperature of the methanol-water solution can be between about −10° C. and about 40° C. Preferably, the temperature of the methanol-water solution is between about 0° C. and about 25° C., and more preferably between about 10° and about 20° C. Preferably, the reaction mixture is predominantly 4,4'-MDDC and the weight of the methanol-water solution is between about five and about ten times the weight of total solids in the mixture.

In order to recover the individual components after washing the mixture with an alcohol or with a methanol-water solution according to the method of this invention, residual alcohol may be separated from the 4,4'-MDDC or solid phase by evaporation and recondensed. The major portion of the alcohol is recovered from the liquid phase by distillation, wherein the extracted constitutents remain as a second solid phase, from which the remaining alcohol may be recovered by evaporation and recondensation. If a methanol-water solution is used, the recondensed methanol may contain water. If such is the case and if it is desired to recover the alcohol undiluted, the water and methanol may be separated by fractional distillation. The recovered alcohol or methanol-water solution may be recycled to a second reaction mixture. This cyclic process may be repeated indefinitely, so that a relatively small quantity of alcohol can be used to recover a relatively large quantity of 4,4'-MDDC.

The invention will now be further illustrated by the following examples.

EXAMPLE 1

From a reaction between formaldehyde and MPC, a reaction mixture was obtained with contained a substantial amount of unreacted MPC, approximately four parts by weight 2,2'-MDDC, twenty-seven parts by weight 2,4'-MDDC, and sixty-nine parts by weight 4,4'-MDDC. The mixture was leached with cold methanol (approximately 20° C.), and then separated by filtration into a filtrate comprising a methanol solution of predominantly MPC, 2,2'-MDDC, and 2,4'-MDDC, and a solid residue of ninety-nine percent by weight 4,4'-MDDC.

EXAMPLE 2

A mixture comprising 52.7 grams of MDDC isomers and higher phenylcarbamate derivatives was washed with cold methanol (approximately 20° C.) and then filtered. The original mixture comprised 35.5 grams of 4,4'-MDDC, 3.5 grams of 2,4' and 2,2'-MDDC, and 13.7 grams of higher phenylcarbamate derivatives. The recovery of washed residue was 31.5 grams, of which ninety-seven percent or 30.5 grams was the 4,4' isomer. The filtrate contained 13.78 grams of higher phenylcarbamate derivatives; and 7.42 grams of MDDC isomers, of which 6.7 grams or ninety percent was the 4,4' isomer.

EXAMPLE 3

From a reaction between formaldehyde and MPC, a reaction mixture was obtained which comprised 429.2 grams of 4,4'-MDDC, 32.98 grams of 2,4'-MDDC and 2,2'-MDDC, 12.6 grams of MPC, 6.2 grams of an unknown reaction intermediate, and forty-six grams of higher phenylcarbamate derivatives. The reaction mixture was leached with a sixty percent methanol - forty percent water solution by volume at 20° C. The solid and liquid phases were separated by filtration. The washed residue comprised four hundred and twenty-nine grams of 4,4'-MDDC, thirty-two grams of 2,4'-MDDC and 2,2'-MDDC, and forty-six grams of higher phenylcarbamate derivatives. The filtrate contained 0.2 grams of 4,4'-MDDC, 0.43 grams of 2,4'-MDDC, 0.55 grams of 2,2'-MDDC, 12.6 grams of MPC, and 6.2 grams of the unknown reaction intermediate.

EXAMPLE 4

Five grams of reaction products from the reaction of MPC and formaldehyde contained 2.78 grams of 4,4'-MDDC, 0.27 grams of 2,4'-MDDC and 2,2'-MDDC, 0.4 grams of higher phenylcarbamate derivatives, 1.05 grams of an unknown reaction intermediate, and 0.5 grams of unreacted MPC. This mixture was leached with isopropyl alcohol at 20° C. The solid and liquid phases were then separated by filtration. The washed solids contained 2.75 grams of 4,4'-MDDC, 0.2 grams of 2,4'-MDDC and 2,2'-MDDC, 0.03 grams of higher phenylcarbamate derivatives, 0.27 grams of the intermediate, and 0.14 grams of MPC. The filtrate contained 0.03 grams of 4,4'-MDDC, 0.07 grams of 2,4'-MDDC and 2,2'-MDDC, 0.37 grams of higher phenylcarbamate derivatives, 0.78 grams of the intermediate, and 0.36 grams of MPC.

EXAMPLE 5

A sample comprising 19.4 grams of methylene diethyl diphenyldicarbamate (approximately ten grams) and higher phenylcarbamate derivatives (approximately nine grams) was washed with methanol at room temperature and then filtered. Approximately 0.38 grams of insoluble residue remained on the filter, comprising about 0.2 grams of methylene diethyl diphenyldicarbamate and about 0.2 grams of higher phenylcarbamate derivatives. The filtrate contained approximately nineteen grams of the original sample, comprising about nine to ten grams of methylene diethyl diphenyldicarbamate and about nine to ten grams of higher phenylcarbamate derivatives.

This wash experiment was repeated, using ethyl alcohol. With this alcohol, the residue comprised about 0.1 grams of total solids, of which about half was methylene diethyl diphenyldicarbamate and about half was higher phenylcarbamate derivatives. The filtrate contained about nineteen grams of the original sample, of which about half was methylene diethyl diphenyldicarbamate and about half was higher phenylcarbamate derivatives.

This example illustrates how a mixture of methylene dimethyl diphenyldicarbamates and other methylene dialkyl diphenyldicarbamates can be separated. By washing the mixture with methyl, ethyl, propyl, or isopropyl alcohol, one would obtain a solid phase including the methylene dimethyl diphenyldicarbamates which are not soluble in the alcohol, and a liquid phase including the alcohol and the other methylene dialkyl diphenyldicarbamates.

While certain representative embodiments and details have been shown for the purpose of illustrating the present invention, it will be apparent to those skilled in the art that various changes and modifications can be made therein without departing from the spirit and scope of the invention.

What is claimed is:

1. A method for the separation of a reaction product, 4,4'-methylene dimethyl diphenyldicarbamate; a reactant, methyl phenylcarbamate; byproduct compounds, or reaction intermediates in the condensation reaction of methyl phenylcarbamate and formaldehyde; other methylene dialkyl diphenyldicarbamates, and other alkyl phenylcarbamates, comprising the steps of:
    (a) washing a mixture, including the methyl phenylcarbamate reactant, byproduct compounds, reaction intermediates, other methylene dialkyl diphenyldicarbamates, or other alkyl phenylcarbamates, and the 4,4'-methylene dimethyl diphenyldicarbamate product, with an alcohol having less than four carbon atoms per molecule, thereby forming a liquid phase which includes the alcohol and the compounds in the mixture which are soluble in the alcohol, and a solid phase of substantially 4,4'-methylene dimethyl diphenyldicarbamate product; and
    (b) separating the solid and liquid phases.

2. The method of claim 1, wherein the byproduct compounds are 2,4'-methylene dimethyl diphenyldicarbamate, 2,2'-methylene dimethyl diphenyldicarbamate, higher phenylcarbamate derivatives, or a mixture thereof.

3. The method of claim 2, wherein the mixture contains a predominant amount of the 4,4'-methylene dimethyl diphenyldicarbamate reaction product.

4. The method of claim 3, wherein the weight of the alcohol is between about five and about ten times the weight of total solids in the mixture.

5. The method of claim 4, wherein the temperature of the alcohol is between about zero and about twenty-five degrees Centigrade.

6. The method of claim 5, which includes a step (c) of recovering the alcohol from the liquid phase.

7. The method of claim 6, wherein the alcohol is recovered by distillation.

8. The method of claim 7, wherein the recovered alcohol is recycled to step (a).

9. The method of claim 8, wherein the alcohol is methanol.

10. A method for the separation of reaction products, the 4,4'-isomer, 2,4'-isomer, and 2,2'-isomer of methylene dimethyl diphenyldicarbamate; a reactant, methyl phenylcarbamate; byproduct compounds, or reaction intermediates in the condensation reaction of methyl phenylcarbamate and formaldehyde; other methylene dialkyl diphenyldicarbamates, and other alkyl phenylcarbamates, comprising the steps of:
    (a) washing a mixture, including the methyl phenylcarbamate reactant, byproduct compounds, reaction intermediates, other methylene dialkyl diphenyldicarbamates, or other alkyl phenylcarbamates, and the 4,4'-isomer, 2,4'-isomer and 2,2'-isomer of the methylene dimethyl diphenyldicarbamate reaction products, with a solution of methanol and water, thereby forming a liquid phase which includes methanol, water, and the compounds in the mixture which are soluble in the methanol-water solution, and a solid phase of substantially 4,4'-isomer, 2,4'-isomer and 2,2'-isomer of the methylene dimethyl diphenyldicarbamate reaction product and
    (b) separating the solid and liquid phases.

11. The method of claim 10, wherein the methanol-water solution comprises a composition of between about sixty percent and about ninety percent methanol and between about ten percent and about forty percent water by volume.

12. The method of claim 11, wherein the mixture contains a predominant amount of 4,4'-methylene dimethyl diphenyldicarbamate.

13. The method of claim 12, wherein the weight of the methanol-water solution is between about five and about ten times the weight of total solids in the mixture.

14. The method of claim 13, wherein the temperature of the methanol-water solution is between about zero and about twenty-five degrees Centigrade.

15. The method of claim 14, which includes a step (c) of recovering the methanol from the liquid phase.

16. The method of claim 15, wherein the methanol is recovered by distillation.

17. The method of claim 16, wherein the recovered methanol is recycled to step (a).

* * * * *